United States Patent [19]

Jadvar et al.

[11] Patent Number: 5,069,215
[45] Date of Patent: Dec. 3, 1991

[54] MULTIPLE ELECTRODE AFFIXABLE SHEET

[75] Inventors: Hossein Jadvar, Chicago; William T. Metzger, Libertyville, both of Ill.

[73] Assignee: Arzco Medical Electronics, Inc., Vernon Hills, Ill.

[21] Appl. No.: 306,997

[22] Filed: Feb. 6, 1989

[51] Int. Cl.$^5$ ............... A61B 5/0402; A61B 8/12; A61N 1/05
[52] U.S. Cl. ............... 128/642; 128/660.03; 128/662.06; 128/784; 128/419 P
[58] Field of Search ............... 128/642, 640, 662.06, 128/784, 786, 419 D, 419 P, 660.03

[56] References Cited

U.S. PATENT DOCUMENTS

| | | | |
|---|---|---|---|
| 3,568,660 | 3/1971 | Crites et al. | 128/786 |
| 3,734,094 | 5/1973 | Calinog . | |
| 3,951,136 | 4/1976 | Wall . | |
| 4,176,660 | 12/1979 | Mylrea et al. . | |
| 4,319,580 | 3/1982 | Colley et al. | 128/661.07 |
| 4,476,872 | 10/1984 | Perlin | 128/642 |
| 4,640,298 | 2/1987 | Pless et al. . | |
| 4,674,518 | 6/1987 | Salo | 128/786 X |
| 4,706,681 | 11/1987 | Breyer | 128/786 X |
| 4,706,688 | 11/1987 | Michael et al. | 128/642 X |
| 4,735,206 | 4/1988 | Hewson . | |
| 4,762,135 | 8/1988 | Puije et al. | 128/784 |
| 4,763,660 | 8/1988 | Kroll et al. | 128/640 |
| 4,817,611 | 4/1989 | Arzbaecher et al. . | |
| 4,834,102 | 5/1989 | Schwarzchild et al. . | |
| 4,852,580 | 8/1989 | Wood . | |
| 4,890,623 | 1/1990 | Cook et al. | 128/642 |

FOREIGN PATENT DOCUMENTS 121090 2/1972 Denmark .
133400 1/1979 Fed. Rep. of Germany .

OTHER PUBLICATIONS

"A Pill Electrode for the Study of Cardiac Arrhythmia", Journal Medical Instrumentation, 1978 by Robert Arzbaecher.
"Use of the Pill Electrode for Transesophageal Atrial Pacing" by Jenkins et al., Journal PACE, 1985.

Primary Examiner—Lee S. Cohen
Attorney, Agent, or Firm—Dressler, Goldsmith, Shore, Sutker & Milnamow, Ltd.

[57] ABSTRACT

A single use disposable esophageal electrode structure is formed with a planar sheet body member. The body member carries a plurality of spaced-apart conductive electrode members. A layer of adhesive on the body member can be used to affix it to an esophageal probe. A plurality of conducting members is coupled to the body member. Each of the conducting members is in turn coupled to a respective one of the electrodes. A free end of the conducting members carries an electrical connector for connection to other electrical units.

32 Claims, 2 Drawing Sheets

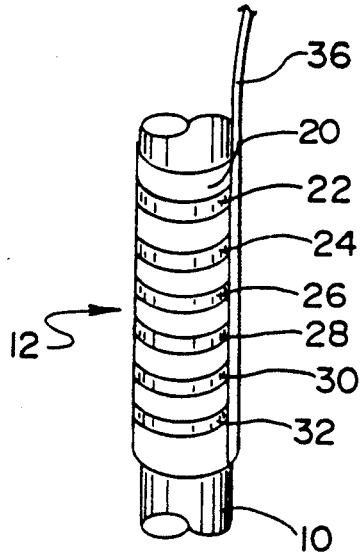
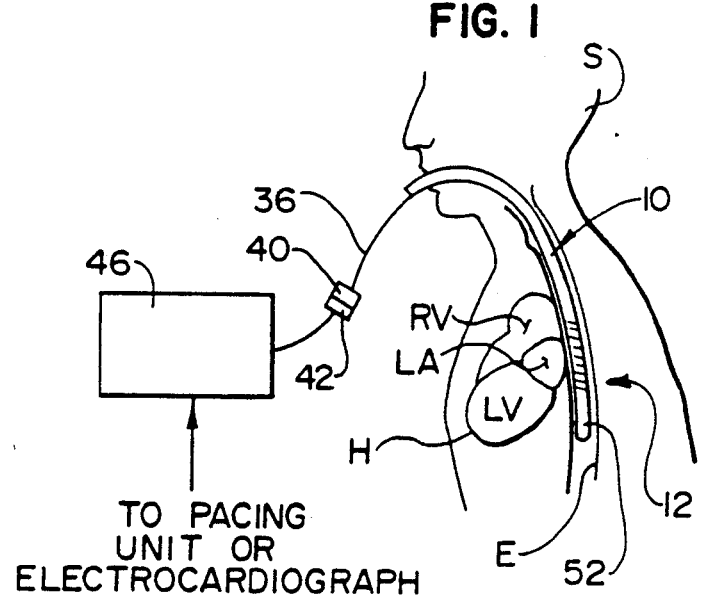
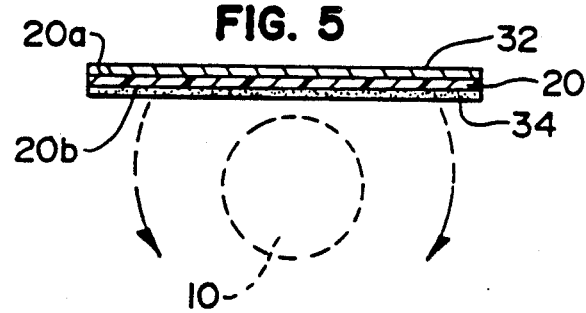

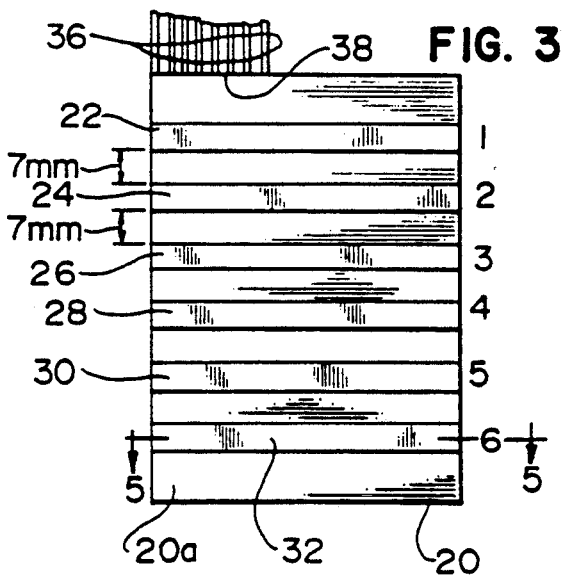
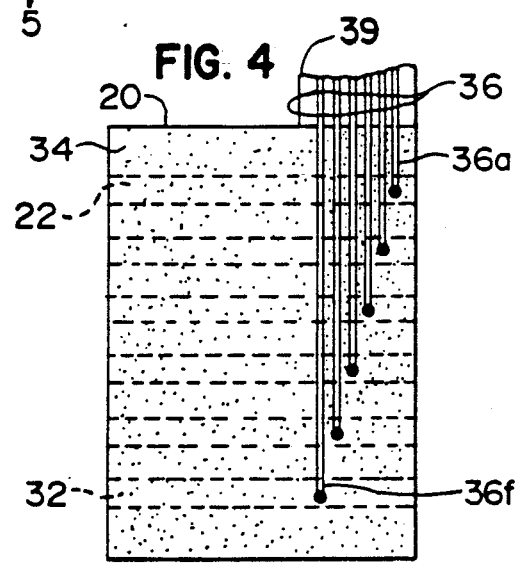
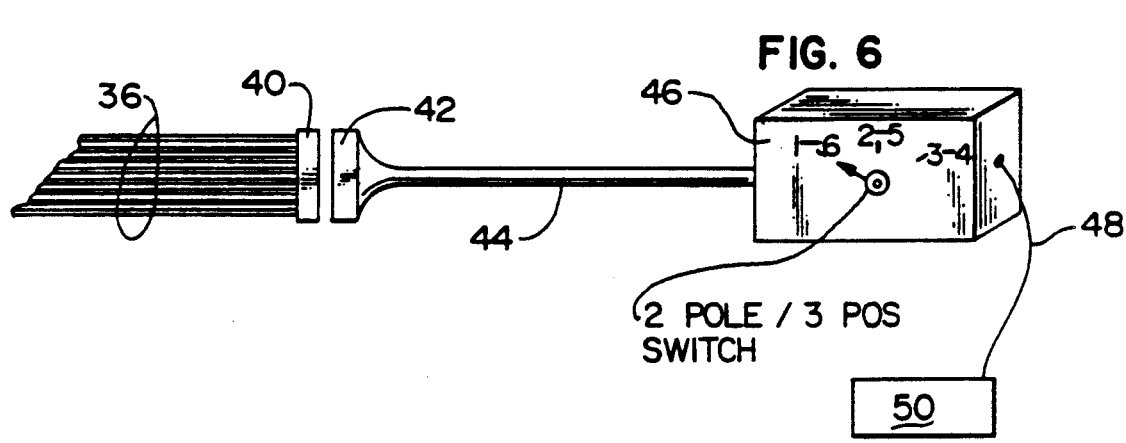

MULTIPLE ELECTRODE AFFIXABLE SHEET

FIELD OF THE INVENTION

The invention pertains to noninvasive cardiac sensing or stimulating. More particularly, the invention pertains to an apparatus and a method for noninvasively pacing a subject's heart while simultaneously conducting for cardiac analysis.

BACKGROUND OF THE INVENTION

It has been recognized that esophageal electrodes are particularly useful in connection with noninvasive esophageal pacing. One such electrode is disclosed for example in co-pending and commonly assigned U.S. Pat. Application Ser. No. 930,748, now U.S. Pat. No. 4,817,611, entitled Esophageal Electrocardiography Electrode.

It has also been recognized that transesophageal electrocardiography can be used for the purpose of studying myocardial One such system is disclosed in commonly copending U.S. Pat. application Ser. No. 267,459 entitled Method and For Detection of Posterior Ischemia.

It has also be recognized that transesophageal echocardiography can be utilized for the purpose of detecting or evaluating among other conditions, myocardial ischemia. It would be desirable to be able to combine the capability of esophageal electrodes and the capability of echocardiography probes into a unit so as to be able to stress the heart and simultaneously study its characteristics.

SUMMARY OF THE INVENTION

An apparatus and met are provided for esophageal heart pacing or monitoring. An apparatus in accordance with invention has a flexible plastic sheet member. The sheet member, which can be generally of a rectangular shape, carries a plurality of spaced-apart electrode members.

A layer of adhesive is carried on the opposite side of the sheet member from the electrodes. Each of the electrodes is connected to one member of a plurality of insulated wires.

The insulated wires can be formed on an elongated MYLAR sheet member which is affixed at one end to the sheet member. At the other end of the elongated MYLAR sheet member is an electrical connector which is in turn connected to each of the conductors of the sheet member.

The electrical connector can in turn be coupled to a switch for selecting various pairs of electrodes. Outputs from or inputs to the selected pair of electrodes can be coupled to or received from an electrocardiograph or an esophageal pacing unit.

Signals from the esophageal pacing unit can be applied to the selected pair of electrodes for the purpose of noninvasively pacing the heart of the subject. Alternately, signals from the selected pair of electrodes can be provided to an amplifier for further processing for the purpose of driving electrocardiograph.

A method of esophageal pacing using a probe insertable into the esophagus of the subject includes the steps of affixing a disposable plurality of electrodes to the probe; positioning the probe in the esophagus; selecting at least one of the electrodes for pacing; and applying a selected electrical pacing signal to at least the selected electrode.

The present esophageal electrode is especially advantageous in that it can be manufactured as a single use element which can be affixed to a reusable probe prior to use. After use, the electrode unit can be discarded.

Alternately, the present multi-electrode structure could be permanently affixed to an esophageal probe. For example, the present electrode structure could be used with an esophageal ultrasonic probe.

Numerous other advantages and features of the present invention will become readily apparent from the following detailed description of the invention and the embodiments thereof, from the claims and from the accompanying drawings in which the details of the invention are fully and completely disclosed as a part of this specification.

BRIEF DESCRIPTION OF THE FIGURES

FIG. 1 is a partial, side, schematic view of a subject illustrating the relationship between a probe in accordance with the present invention and the heart of the subject;

FIG. 2 is an enlarged portion of a probe carrying a multi-element electrode in accordance with the present invention;

FIG. 3 is an elevational view of one side of a disposable multi-electrode esophageal unit;

FIG. 4 is a second view of the disposable multi-electrode esophageal unit of FIG. 3;

FIG. 5 is a sectional view taken along plane 5—5 of FIG. 1; and

FIG. 6 is a pictorial diagram of an electrode selecting switch in accordance with the present invention.

DETAILED DESCRIPTION OF THE PREFERRED EMBODIMENT

While this invention is susceptible of embodiment in many different forms, there is shown in the drawing and will be described herein in detail a specific embodiment thereof with the understanding that the present disclosure is to be considered as an exemplification of the principles of the invention and is not intended to limit the invention to the specific embodiment illustrated.

FIG. 1 illustrates a subject S having a heart H and an esophagus E with a probe 10 positioned therein. The probe 10 carries a disposable esophageal electrode structure 12. The structure 12 is formed with a flexible medical grade plastic base member 20. The base member 20 carries a plurality of spaced-apart conducting elements 22–32 on a surface 20a.

Each of the elements 22–32 is formed of a biocompatible conducting material. Each of the elements 22–32 is permanently affixed to the base member 20. The base member 20 on a surface 20b opposite the surface 20a carries a layer of adhesive 34. The layer of adhesive 34 is used to affix the member 20 to the reusable probe 10.

The adhesive layer 34 can be formed of any biocompatible adhesive with adequate strength so as to fix the electrode structure 12 to the probe 10 for the length of any desired procedure. Subsequent to completion of the desired procedure, the electrode structure 12 is removed from the probe 10 and disposed of. The probe 10 can then be sterilized and reused.

A plurality of conducting members 36 is attached in a region 38 to the member 20. The plurality 36 can be formed with a plastic base member 39 on which is deposited a plurality of spaced apart conducting traces 36a–36f. Each of the traces, such as the trace 36a is electrically connected to a respective one of the conducting members 22–32, such as the member 22.

It will be understood that the details of the formation of the traces 36a–36f and the way in which those traces are carried by the plastic member 39 are not limitations of the present invention. Similarly, the details of how the traces 36a–36f interconnect with the conducting members 22–32 are also not a limitation of the present invention.

A second end of the plurality 36 carries an electrical connector 40 of a conventional variety. The connector 40 can be mated with a corresponding connector 42 which is carried by a multiple conductor cable 44. The cable 44 is in turn coupled to a manually operable switch 46.

The switch 46 could for example be implemented as a two-pole three position switch. It will be understood that the exact details of the switch 46 are not a limitation of the present invention. The switch 46 is used to manually select a pair of electrodes from the plurality 22–32. Output from the selected pair of electrodes, or input thereto, on a two-conductor cable 48 can be coupled to an ECG or received from an esophageal pacing unit 50.

The disposable multi-electrode element 12, in combination with the probe 10, makes it possible to combine cardiac pacing as a form of stress simultaneously with echocardiography to determine and sense heart function. For example, if the probe 10 is a transesophageal ultrasonic probe of a type marketed by Hoffrel Instruments, Inc., Model 482, the electrode structure 12 can be used for pacing the left atrium of the heart H. Simultaneously, an ultrasonic transmitter and receiver 52 on the probe 10 transmits ultrasonic waves toward the heart H and senses ultrasonic reflections therefrom for the purpose of forming an image of the cardiac chambers as the heart H is being simultaneously stimulated.

In a typical procedure, the sheet electrode member 12 is affixed to the perimeter of the probe 10 using the layer of adhesive 34. The electrode structure 12 is located at a level about 10 centimeters above the ultrasonic transmitter and receiver 52 in the probe.

The ultrasonic transmitter/receiver 52 is carried at a distal end of the probe 10. The multi-electrode element 12 is carried on the probe 10 adjacent the transmitter/receiver 52 but spaced therefrom.

The probe 10 is inserted in a conventional fashion into the esophagus E of the subject S. The electrode structure 12 is then connected via connectors 40, 42 to switch selector 46. The appropriate electrodes are selected and then either an esophageal preamplifier or a pacing unit is coupled to the cable 48 for sensing signals from or for pacing the heart H.

By way of example and not by wy of limitation, the width of each of the electrode members 22–32 can be on the order of 7 millimeters with a corresponding spacing therebetween. The length dimension of the sheet member 20 can be on the order of 63 millimeters and the width dimension can be on the order of 40 millimeters.

The length of the plastic extension member 40, which could be formed of MYLAR can be on the order of 50 centimeters. The body member 20 can also be formed of a MYLAR sheet. It will be understood that any medical grade plastic could be used for the body member 20 without departing from the spirit and scope of the present invention.

Further, in a typical installation the switching unit 46 can be connected so as to switch as electrode pairs, electrodes 22, 32; 24, 30; or 24,26.

Alternately, the multiple electrode system 12 can be fabricated permanently attached to an imaging probe. Imaging probes, of the type discussed above, usually include an ultrasonic transmitter and receiver located at the end of the probe.

The transmitter is located in the esophagus below the heart and is oriented on the probe to transmit toward the heart. Reflected ultrasonic waves are detected by the transceiver, converted to corresponding electrical signals and transmitted from the probe to outside analysis circuitry.

Hence, it will be understood that the multiple electrodes 22–32 could be permanently attached to the body of the esophageal ultrasonic probe as generally indicated in FIG. 1.

From the foregoing, it will be observed that numerous variations and modifications may be effected without departing from the spirit and scope of the novel concept of the invention. It is to be understood that no limitation with respect to the specific apparatus illustrated herein is intended or should be inferred. It is, of course, intended to cover by the appended claims all such modifications as fall within the scope of the claims.

We claim:

1. A multi-element electrode structure removably affixable to an essentially cylindrical esophageal probe which can then be inserted into the esophagus of a patient, the electrode structure comprising:
   a rectangular insulative sheet member having a selected length dimension and a width dimension corresponding to the perimeter of the esophageal probe;
   a plurality of spaced electrodes carried by said sheet member;
   adhesive means carried by said sheet member for removably affixing said member to the probe; and
   a plurality of elongated conducting members with each said conducting member having an end in electrical contact with a respective one of said electrodes.

2. A multi-element electrode as in claim 1 with said plurality of elongated conducting members carrying an electrical connector displaced from said sheet member.

3. A multi-element electrode as in claim 1 with said sheet member formed of a selected plastic.

4. A multi-element electrode as in claim 2 including means, couplable to said connector, for electrically selecting at least one of said electrodes.

5. A multi-element electrode as in claim 2 including means, for electrically selecting at least first and second of said electrodes.

6. A method of sensing information from the heart of a subject comprising:
   providing a reusable esophageal probe with an exterior housing;
   removably affixing a disposable plurality of single-use electrodes to the exterior housing of the probe;
   positioning the probe in the esophagus;
   selecting at least one of the electrodes; and
   sensing, using the selected electrode, electrical signals generated by the heart of the subject.

7. A method as in claim 6 including removing the probe from the esophagus and then removing the plurality of electrodes from the housing of the probe.

8. An esophageal pacing probe usable to pace the heart of a patient comprising:
   an elongated body portion having a proximal end and a distal end;
   an ultrasonic transmitter carried on said distal end;
   a plurality of spaced-apart electrodes carried on said body portion between said proximal end and said transmitter but spaced therefrom thereby providing for independent positioning of said transmitter and a selected pacing electrode with respect to the patient's heart.

9. An esophageal probe as in claim 8 including a layer of adhesive between said body portion and said electrodes.

10. An esophageal probe as in claim 9 with said plurality of electrodes removably attached to said body portion.

11. An esophageal probe as in claim 9 with said plurality of electrodes fixedly attached to said body portion.

12. An esophageal probe as in claim 8 with said plurality of electrodes fixedly attached to said body portion.

13. An esophageal probe as in claim 8 connectable to an external electrical device and including means, coupled to said transmitter and extending to said proximal end of said body portion, for connection to the external electrical device.

14. An esophageal probe as in claim 13 including an ultrasonic receiver carried on said distal end of said body portion.

15. An esophageal probe as in claim 8 including means for electrical conduction coupled to at least some members of said plurality of electrodes and extending to said proximal end of said body portion.

16. An esophageal probe as in claim 8 including means, couplable to said proximal end of said body portion, for selecting first and second electrodes from said plurality of electrodes.

17. An esophageal probe comprising:
   an elongated body having a proximal end and a distal end;
   an imaging transmitter/receiving carried on said distal end;
   a plurality of spaced-apart electrodes usable for esophageal pacing affixed to said body between said proximal end and said transmitter/receiver with at least some of said electrodes located about 10 centimeters from said transmitter/receiver; and
   means for electrically coupling to and selecting at least some of said electrodes.

18. An esophageal probe as in claim 17 with said plurality of electrodes carried on a non-conducting member affixed to said body.

19. An esophageal probe as in claim 17 with said coupling means including a plurality of elongated conducting members for conveying electrical signals to and from said electrodes.

20. An esophageal probe as in claim 17 with said body being generally cylindrical and with said electrodes forming a plurality of circumferential conductors around said cylindrical body.

21. A multi-function cardiac imaging probe insertable into the esophagus of a subject adjacent a posterior heart surface and couplable to an exterior electrical pacing unit comprising:
   an elongated body having a proximal end and a distal end with said distal end insertable into the esophagus;
   an ultrasonic heart function imaging transmitter/receiver carried on said distal end;
   a plurality of more than two spaced-apart conductive members carried on said distal end adjacent to, but spaced from said transmitter/receiver toward said proximal end;
   means for selecting a pacing electrode from said plurality;
   a plurality of elongated conductive wires carried by said body with each said wire having a proximal end and a distal end, each said distal end coupled to a respective one of said conductive members with said proximal ends coupled to aid selecting means, said selecting means couplable to the exterior electrical pacing unit and with both said transmitter/receiver and said selected electrode independently located with respect to the heart.

22. A method of cardiac imaging of a subject using a multi-function esophageal probe which carries an imaging transmitter/receiver at a distal end thereof and a plurality of electrodes adjacent to but spaced from the transmitter/receiver, the method comprising:
   inserting the distal end into the esophagus of the subject;
   locating the transmitter/receiver to carry out a selected imaging function and in response to the locating step,
   selecting a pair of pacing electrodes from among the members of the plurality of electrodes; and
   providing pacing electrical signals to the selected electrodes while simultaneously carrying out the imaging function.

23. A method of sensing information from the heart of a subject comprising:
   providing a reusable esophageal probe with an exterior housing and with a transmitter/receiver carried on a distal end thereof;
   affixing a plurality of electrodes to the exterior housing of the probe adjacent to the distal end and spaced from the transmitter/receiver;
   positioning the distal end of the probe in the esophagus;
   generating cardiac images using the transmitter/receiver;
   selecting at least one of the electrodes; and
   using the selected electrode to apply, electrical signals for pacing to the heart of the subject simultaneously wit generating the cardiac images.

24. A method as in claim 23 including removing the probe from the esophagus and the removing the plurality of electrodes from the housing of the probe.

25. An esophageal imaging probe insertable, at last in part into the esophagus of a patient and extending adjacent a posterior surface of the patient's heart comprising:
   an insertable elongated body portion having a proximal end and a distal end;
   an ultrasonic imaging transmitter carried on said distal end;
   a plurality of spaced-apart pacing electrodes carried by said body portion adjacent said transmitter but spaced therefrom toward said proximal end with said plurality of electrodes and said body portion coupled together by at least one layer of adhesive with at least a first electrode independently selectable from said plurality to carry out a heart pacing function simultaneously with said imaging transmitter carrying out a heart imaging function.

26. An esophageal probe as in claim 25 with said plurality of electrodes removably coupled to said body portion.

27. An esophageal probe as in claim 25 with said plurality of electrodes fixedly coupled to said body portion.

28. An esophageal probe as in claim 25 connectable to an external electrical pacing device and including means, coupled to said electrodes and extending to said proximal end of said body portion, for connection to the external electrical device.

29. An esophageal probe as in claim 25 including manually adjustable means, couplable to said proximal end of said body portion, for selecting said first and a second pacing electrode from said plurality of electrodes.

30. An esophageal probe comprising:
an elongated body having a proximal end and a distal end;
an imaging transmitter/receiver carried on said distal end;
a plurality of spaced-apart electrodes usable for esophageal pacing supported on said body adjacent to but spaced from said transmitter/receiver toward said proximal end; and
means for electrically coupling to and selecting at least a first of said electrodes spaced from said imaging transmitter/receiver for carrying out a heart imaging function simultaneously with a pacing function with said electrodes and said body joined together by at least one adhesive layer.

31. An esophageal pacing/imaging probe useable with a source of electrical pacing signals and insertable, at least in part, into an esophagus of a subject, adjacent the subject's heart comprising:
an elongated body portion having a proximal end and a distally located region insertable into the esophagus;
an ultrasonic transmitter carried on said insertable region;
a plurality of esophageal pacing electrodes carrie don said insertable region, displaced from said transmitter a selected distance; and
switch means for selecting first and second pacing electrodes from said plurality and for coupling electrical pacing signal thereto from the source for pacing signals with said transmitter and said selected electrodes each independently located relative to the patient's heart to carry out respectively a heart imaging function and a heart pacing function.

32. An esophageal pacing/imaging probe useable with a source of pacing signals and insertable, at least in part, into an esophagus of a subject, adjacent the subject's heart and usable with a switch for selecting at least one pacing electrode and for coupling electrical pacing signal thereto from the source of pacing signals the probe comprising:
an elongated body portion having a proximal end and a distally located region insertable into the esophagus;
an ultrasonic transmitter carried on said insertable region; and
a plurality of esophageal pacing electrodes carried on said insertable region, displaced from said transmitter a selected distance toward said proximal end and couplable to the switch with both said transmitter and said selected electrode independently locatable relative to the patient's heart to carry out respectively a heart imaging function and a heart pacing function.

* * * * *

UNITED STATES PATENT AND TRADEMARK OFFICE
CERTIFICATE OF CORRECTION

PATENT NO.  : 5,069,215

DATED       : December 3, 1991

INVENTOR(S) : Hossein Jadvar, et al.

It is certified that error appears in the above-identified patent and that said Letters Patent is hereby corrected as shown below:

```
Col. 1, line 22, after "myocardial" insert --ishemia.--.
Col. 1, line 23, before "copending" insert --assigned
                 and--.
Col. 1, line 24, after "and" insert --Apparatus--.
Col. 1, line 36, "met" should be --method--.
Col. 1, line 37, after "or" insert --heart--.
Col. 1, line 38, after "with" insert --the--.
Col. 3, line 56, "wy" should be --way--.

Col. 5, line 44, "receiving" should be --receiver--.
Col. 6, line 16, "aid" should be --said--.
Col. 6, line 51, "wit" should be --with--.
Col. 6, line 55, "last" should be --least--.
Col. 8, line  8, "carrie don" should be --carried on--.
Col. 8, line 24, "signal" should be --signals--.
```

Signed and Sealed this

Twentieth Day of December, 1994

Attest:

BRUCE LEHMAN

*Attesting Officer*　　　*Commissioner of Patents and Trademarks*